United States Patent [19]

Chiu

[11] Patent Number: 6,153,802
[45] Date of Patent: Nov. 28, 2000

[54] LIQUID-FLUORINATION SYSTEM AND METHOD

[75] Inventor: Yuon Chiu, Morris County, N.J.

[73] Assignee: AlliedSignal Inc., Morristown, N.J.

[21] Appl. No.: 09/075,486

[22] Filed: May 8, 1998

[51] Int. Cl.[7] .............................. C07C 17/00; B01D 3/14
[52] U.S. Cl. ............................................ 570/123; 202/182
[58] Field of Search .................................... 570/167, 168, 570/123; 202/182

[56] References Cited

U.S. PATENT DOCUMENTS

| | | | |
|---|---|---|---|
| 2,005,709 | 6/1935 | Daudt et al. | |
| 2,749,374 | 6/1956 | Ruh et al. | |
| 2,749,375 | 6/1956 | Ruh et al. | |
| 4,091,043 | 5/1978 | Ohsaka et al. | |
| 5,457,267 | 10/1995 | Jansen et al. | 588/206 |
| 5,534,118 | 7/1996 | McCuaden | 202/205 |
| 5,563,393 | 10/1996 | Felix et al. | |
| 5,574,192 | 11/1996 | VenDerPuy et al. | 570/167 |

FOREIGN PATENT DOCUMENTS

| | | |
|---|---|---|
| 6-24419 | 2/1994 | Japan. |
| 1153712 | 5/1969 | United Kingdom. |
| WO96/01241 | 7/1995 | WIPO. |
| WO95/35271 | 12/1995 | WIPO. |
| WO96 05156 | 2/1996 | WIPO. |
| WO98 00378 | 1/1998 | WIPO. |

*Primary Examiner*—Elli Peselev
*Attorney, Agent, or Firm*—Colleen D. Szuch; Jay P. Friedenson

[57] ABSTRACT

A system and process for producing a fluorinated organic compound, said process comprising (a) reacting an organic compound with a fluorinations agent in the presence of a liquid-phase fluorinations catalyst to produce a product stream; (b) scrubbing said product stream to remove a substantial portion of said catalyst to form a low-catalyst content product stream; and (c) recovering said fluorinated organic compound from said low-catalyst content stream.

26 Claims, 2 Drawing Sheets

LIQUID-FLUORINATION SYSTEM AND METHOD

FIELD OF INVENTION

The present invention relates to fluorinations systems and methods. More specifically, the present invention relates to a liquid-phase fluorinations system and method for reducing corrosion and facilitating heat transfer.

BACKGROUND OF THE INVENTION

Liquid-phase fluorinations involves the use of a mixture of corrosive reaction materials. The corrosion is acute, especially where Lewis-acid catalysts, such as antimony halide catalysts, are used under high reaction pressures and at elevated temperatures. Under these conditions, strong acids form which tend to corrode reactor vessels, even those comprised of corrosion-resistant materials such as Inconel 600, NAR25-50MII, Hastelloy C, Hastelloy G-30, duplex stainless steel, and Hastelloy C-22. Reactor corrosion compromises the structural integrity of the reactor and reduces its useful life.

Liquid-phase fluorinations also requires the constant input of heat. Traditionally, the amount of heat transferred to the reactor should be sufficient not only to drive the fluorinations reaction, but also to provide the heat necessary for distillation of the vapor product stream produced by the reaction. The heat for distillation and other post-reaction processing is transferred through the reactor vessel because the vaporized product stream generally is considered too corrosive for reboilers and other post-reaction heating apparatus. Conventional techniques for inputting heat to the reactor vessel include, for example, employing heating jackets and/or internal coils, and preheating and vaporizing the reaction materials.

For highly corrosive reactions, such as the synthesis of 1,1,1,3,3, pentafluoropropane (HFC-245 fa), traditional heat input techniques tend to be inadequate. Often, in such applications, the reactor vessel is lined with a corrosion-resistant fluoropolymer which unfortunately is a thermal insulator that impedes the transfer of heat into the reactor.

Aside from the problems of heat input into the reactor, it is frequently preferable to minimize heat flux or skin temperature in a reactor vessel containing corrosive reactants. The input of heat to a reactor vessel in excess of that needed for the reaction tends to vaporize catalyst and increase the corrosive nature of the product stream. Moreover, the additional heat leads to an increase in the thermal breakdown of reactants and/or products and in the formation of by-products.

Therefore, there is a need for a liquid-phase fluorinations system and method which minimizes corrosion while allowing for the controlled input of heat. The present invention fulfills this need among others.

BRIEF DESCRIPTION OF DRAWINGS

The invention may best be understood by reference to the following description taken in conjunction with the accompanying drawings, wherein like reference numerals identify like elements, and wherein.

DESCRIPTION OF THE INVENTION AND PREFERRED EMBODIMENTS

Figure 1:
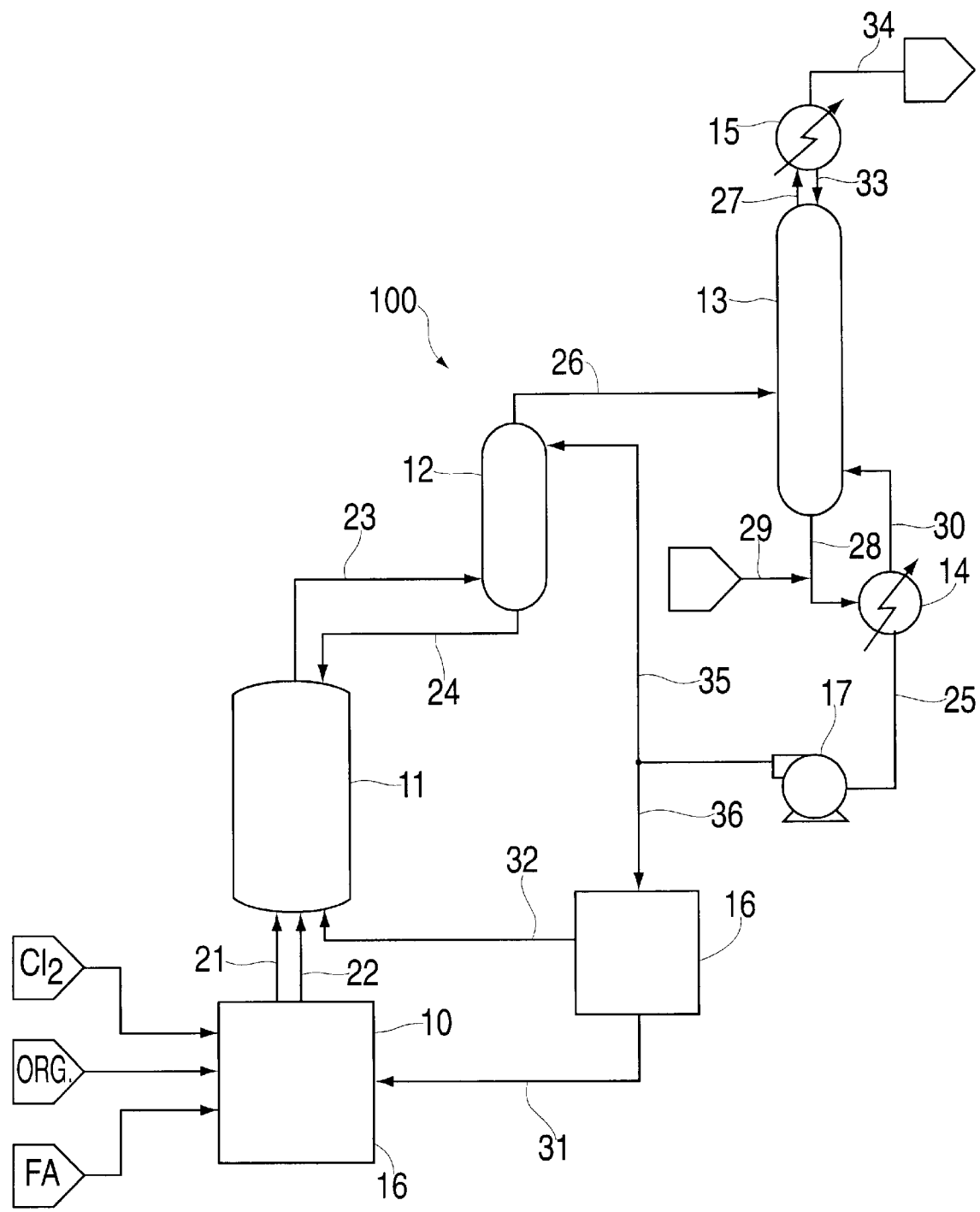
FIG. 1 shows a schematic diagram of a preferred a liquid-fluorinations system.

The present invention provides for a liquid-phase fluorinations system and method which facilitates heat input and minimizes corrosion by scrubbing the vaporized product stream leaving the reactor. Scrubbing readily removes a significant portion of high-boiling point components from the product stream. Among these components, is vaporized catalyst which tends to be particularly corrosive. Therefore, rather than removing the catalyst from the product stream during distillation of the desired product, as is done traditionally, a prescrubber is used to remove it as the product stream leaves the reactor. This way, a significant portion of the corrosion causing material is removed from the product stream early in the process and relatively easily as compared to traditional distillation techniques.

By removing the catalyst vapor as the product stream leaves the reactor, post-reaction processing is less corrosive. Reduced corrosion allows for reboilers and other post-reaction apparatus that can be used to input heat into the system. This post-reaction heating relieves the need to input heat through the reactor vessel in excess of that needed for the reaction to support distillation. Additionally, the heat added in post-reaction processing is typically returned to the reactor with one or more feedback streams thereby supplementing the heat input to the reactor.

One aspect of the invention comprises a process for the liquid-phase fluorinations of an organic compound. In a preferred embodiment, the process comprises (a) reacting an organic starting material with a fluorinations agent in the presence of a liquid-phase fluorinations catalyst to produce a product stream; (b) scrubbing said product stream to remove a substantial portion of said catalyst to form a low-catalyst content product stream; and (c) recovering desired fluorinated product(s) from said low-catalyst content stream.

Another aspect of the invention comprises a reactor system for performing the above-mentioned process. In a preferred embodiment, the reactor system comprises (a) means for reacting an organic starting material with a fluorinations agent in the presence of a liquid-phase fluorinations catalyst to produce a product stream; (b) means for scrubbing said product stream to remove a substantial portion of said catalyst to form a low-catalyst content product stream; and (c) means for recovering desired fluorinated products from said low-catalyst content product stream.

Yet another aspect of the invention is a prescrubber which can be incorporated into new fluorinations systems or retrofitted to existing systems. In a preferred embodiment, the prescrubber comprises (a) means for receiving a vapor product stream from a fluorinations reaction; (b) means for receiving a liquid scrubbing stream; (e) means for contacting said liquid stream and said vapor stream such that a high-boiling component is removed from the product stream to form a low-catalyst content product stream; and (d) means for outputting said low-catalyst content product stream.

Referring to FIG. 1, a preferred embodiment of a reactor system 100 of the present invention is shown. The reactor system 100 comprises a reactor vessel 11, a prescrubber 12, a distillation unit 13, and an optional preconditioning system 10 and vaporizer 16. Depending upon the heating requirements, the optional preconditioner system 10 may be used to preheat a liquid stream 21 and to vaporize and superheat a vapor stream 22. Streams 21 and 22 are fed into the reactor vessel 11.

Liquid-phase fluorinations within reactor vessel 11 produces a vaporized product stream 23 which is fed into the catalyst prescrubber 12. A scrubbing liquid is used to scrub catalyst from the product stream 23 to form a low-catalyst content product stream 26. A substantial amount of scrubbed catalyst is returned to the reactor vessel by the scrubbing liquid in return stream 24.

The low-catalyst content stream 26 is fed to the distillation unit 13. Using conventional distillation techniques, the distillation unit generates a low-boiling fraction stream 27 and a high-boiling fraction stream 28. Preferably, a portion of the high-boiling fraction stream 28 is vaporized in a reboiler 14 and returned to the distillation unit 13 in vapor stream 30. Another portion of the high-boiling fraction stream 28 leaves the reboiler 14 as a liquid in recycle stream 25. At this point, it may be advantageous to use a pump 17 if gravity is not sufficient to move the stream. Preferably, a portion 35 of the recycle stream 25 is used as the scrubbing liquid in prescrubber 12. The remaining portion 36 may be fed to optional vaporizer 16.

The vaporizer 16 vaporizes a portion of the recycle stream 25 and which is emitted in the form of a recycled vapor stream 31 and a recycled liquid stream 32. The recycled liquid stream 32 inherently contains the high-boiling materials of recycle stream 25, which usually include the catalyst, and is returned to the reactor vessel 11. Before being returned to the reactor vessel 11, the recycled vapor stream 31 preferably is superheated in preconditioner 10 to add heat to the reaction.

Referring back to the distillation unit 13, the low-boiling fraction stream 27 leaving the distillation unit 13 encounters a condenser 15 which returns a portion of the stream back to the distillation unit as reflux 33. The remaining portion leaves the condenser 15 as stripped product stream 34. The desired product is recovered from this stream using conventional techniques, typically distillation.

The reaction system 100 and method of using it are described below in greater detail and with respect to preferred and alternative embodiments.

The reactor vessel 11 facilitates liquid-phase fluorinations and may comprise any apparatus conventionally used for preparing fluorinated compounds by liquid-phase fluorinations. Such apparatus are well known and may consist of one or more reactor vessels depending upon desired reaction rates and economic constraints. An example of a satisfactory apparatus for this purpose is a single reaction vessel, such as autoclave, to which the reaction materials can be added, in liquid or gaseous form, and heated well enough to control reaction temperature. The heating may be performed by preconditioning the reaction materials, and/or by equipping the reactor vessel with a heating jacket or internal coil.

The reaction vessel 11 should be capable of sustaining reaction pressures up to about 300 psi or whatever the maximum reaction pressure is expected to be. Because the reaction typically takes place under pressure, the reactor vessel is generally comprised of metal or other structurally rigid material. Suitable materials include, for example, carbon steel, stainless steel, Inconel alloy, Monel alloy, Hastelloy, or other type of a structurally suitable alloy.

Preferably, reactor vessel 11 is lined with a fluoropolymer for corrosion resistance. As used herein, the terms "fluorinated polymer" and "fluoropolymer" are used interchangeably and broadly refer to any polymer, copolymer or blend of polymers having a fluoride atom in at least one of the monomers. Preferred materials include, for example, polytetrafluoroethylene, poly(vinylidene fluoride), ethylene-tetrafluoroethylene polymer, ethylene-hexafluoropropylene polymer, tetrafluoroethylene-hexafluoropropylene polymer, perfluoroalkoxy polymer, any modified version of the above-mentioned polymers, and blends of two or more thereof. The polytetrafluoroethylene or its modified version is particularly preferred.

The reactor vessel 11 facilitates fluorinations by operating under conditions sufficient to react reaction materials in the presence of a liquid-phase fluorinations catalyst. The reaction materials include one or more organic starting materials and a fluorinations agent. Additionally, a recycle stream may be used to supplement the feed.

The organic starting material may be any compound that contains a carbon-bonded chlorine or other atom replaceable by fluorine and/or that contains a carbon-carbon unsaturated bond that is saturatable with fluorine. Suitable organic starting materials include, without limitation, chlorinated hydrocarbon compounds containing from 1 to 6 carbon atoms and 1 to 12 chlorine atoms. A A A preferred organic starting material has the formula $C_wH_xCl_yF_z$, wherein w is 1 to about 5, and with the previsos 2w+2=x+y+z and 0<y. More preferrably, the organic starting material has the formula $CF_aCl_{3-a}CH_2CHF_bCl_{2-b}$, wherein b=0 or 1, and a=0 to 3 (see also, U.S. Pat. No. 5,574,192). The most preferred starting material is 1,1,1,3,3 pentachloropropane (HCC-240).

Suitable fluorinations agents include any material that provides a fluorine atom for fluorinations of the organic starting material. Preferred fluorinations agents include hydrogen fluoride, elemental fluorine, and boron trifluoride. The most preferred agent is hydrogen fluoride.

Any suitable fluorinations catalyst may be used including, without limitation, halides and mixed halides of antimony, niobium, arsenic, tin, titanium and tantalum and combinations of two or more thereof. Pentavalent antimony, niobium, arsenic and tantalum halides are commercially available and mixed halides thereof are created in situ upon reaction with hydrogen fluoride (see U.S. Pat. No. 5,574, 192). Antimony pentachloride is more preferred because of its low cost and availability. Pentavalent antimony mixed halides of the formula $SbCl_2F_3$ and $SbBi_2F_3$ where n is 0 to 5 are even more preferred. Although the amount of fluorinations catalyst used may vary widely, it is believed that, for most applications, suitable results can be obtained when the weight percent of catalyst relative to the organics is from about 1 to about 75%, preferably from about 5 to about 50%, and more preferably from about 10 to about 25%.

It may be advantageous to periodically regenerate the catalyst. Procedures for doing this are known in the art. For example, the catalyst may be regenerated by feeding an oxidizing agent, such as chlorine, to the reactor vessel 11 in an amount from about 1 to about 10 mole percent relative to the amount of catalyst initially present in the reactor vessel. The oxidizing agent may be continuously or intermittently added. One of ordinary skill in the art can readily determine the amount of agent to be added to optimize the use of the catalyst.

The reaction conditions required to facilitate liquid-phase fluorinations typically involve elevated pressures and temperatures. The reaction pressure can vary and optimal pressures can be determined by someone skilled in the art without undue experimentation. It has been found that, in most applications, suitable results can be obtained when operating pressures range from about 30 to about 300 psi, preferably from about 70 to about 260 psi, and more preferably from about 100 to about 200 psig. The reaction temperature generally is from about 70 to about 350° F., and preferably from about 150 to 250° F.

Reaction times are dependent on several factors including catalyst concentration, the type of catalyst, and the temperature. For a batch process, the progress of the reaction can be monitored conveniently by the increase in pressure due to the formation of by-product HCL. Typical reaction times range from about 1 to about 25 hours, and preferably from about 2 to about 8 hours. For a continuous process, the reaction times ranges from about 1 minute to about 5 hours, and, preferably, from about 10 minutes to about 1 hour.

The product stream 23 leaving the reactor vessel 11 enters the prescrubber 12. The catalyst pre-scrubber removes a substantial portion of the entrained or gaseous catalyst complex from the product stream 23. Preferably, this catalyst complex is returned to the reactor vessel 11, and even more preferably, it is returned by gravity. In the latter embodiment, it may be preferable to have the prescrubber 12 mounted atop the reactor 11. The prescrubber also removes other entrained or gaseous high-boiling point components. The bulk removal of the catalyst and other high-boiling point components in the prescrubber reduces the corrosiveness of the product stream which in turn allows for post-reaction apparatus such as reboilers and recycle preconditioners.

Suitable prescubbers include any apparatus that removes a high-boiling point component from a vapor feed by contacting it with a liquid having little or no partial pressure of the high-boiling point component. In a preferred embodiment, the prescrubber comprises (a) means for receiving a vapor product stream from said reaction vessel; (b) means for receiving a liquid scrubbing stream; (c) means for contacting said liquid stream and said vapor stream such that a high-boiling component is removed from the product stream to form a low-catalyst content product stream; and (d) means for outputting said low-catalyst content product stream.

Figure 2:
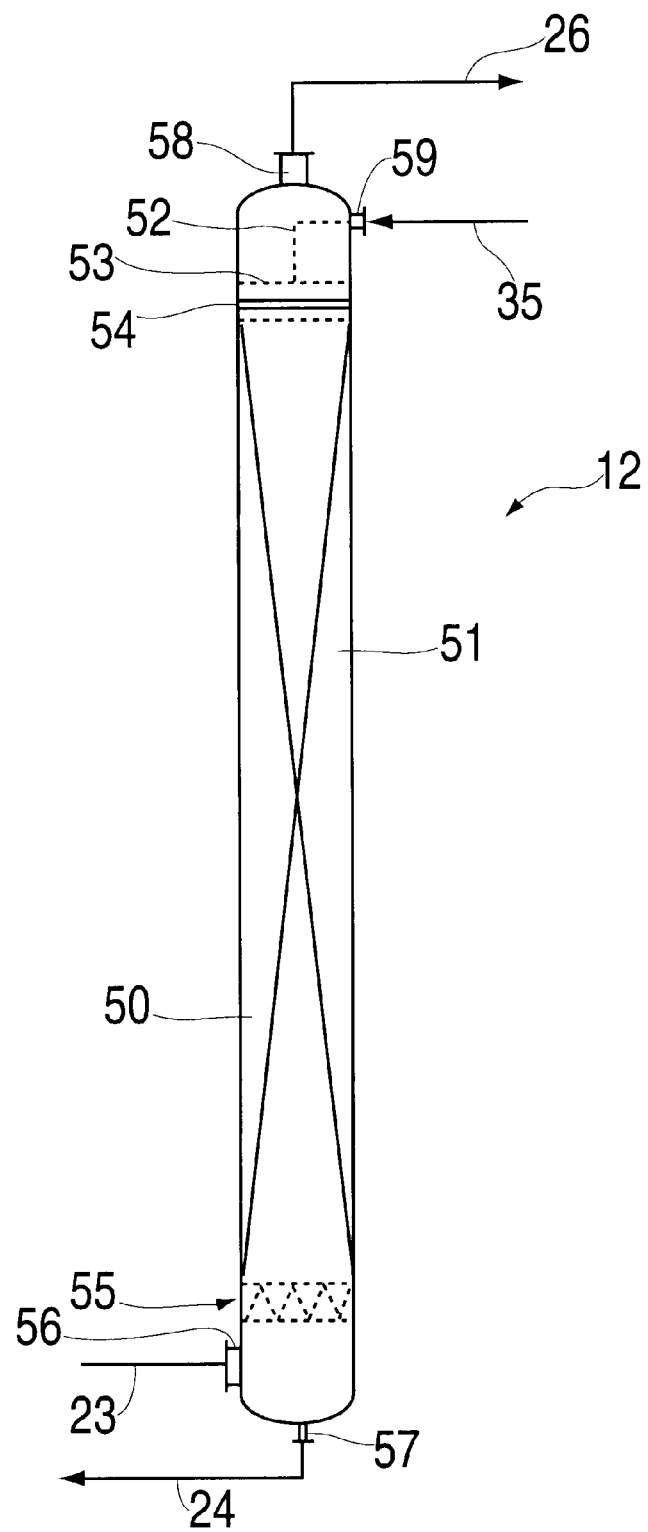
FIG. 2 shows a side view of a preferred prescrubber apparatus.

A preferred prescrubber is depicted in FIG. 2. As shown, the prescrubber 12 comprises a substantially cylindrical column 50 that receives the vaporized product stream 23 through a gas inlet 56 and the scrubbing liquid 35 through a liquid inlet 59. The prescrubber outputs the liquid return stream 24 through the liquid drain 57 and the low-catalyst content product stream 26 through the gas outlet 58. The column 50 contains a packing support 55 and a packing hold down 54 to accommodate packing 51. Any conventional packing, such as pall rings, may be used. To control the flow of scrubbing liquid over the packing 5 1, a liquid feed line 52 and liquid distributer 53 may be employed. In applications involving particularly corrosive catalysts, the prescrubber is preferably lined, coated, or otherwise protected by a fluoropolymer as defined above.

The particular size and operating parameters of the pre-scrubber depend upon the product being synthesized and the equipment available. For example, in the production of 245 fa, an 18 foot by 2 foot prescrubber (manufactured by Edlon, Philadelphia, Pa.) is used with 2 inch pall rings packing (manufactured by Koch Engineering, Wichita, Kans.). The prescrubber operates at a pressure less than the reaction pressure, preferably less than about 1 to about 10 psia. In one particular synthesis of 245 fa, the prescrubber operates at a pressure of about 160 psig which was about 2 psia less than reaction pressure. The temperature of the prescrubber was about 200° F. at the bottom and slightly less at the top.

The scrubbing liquid preferably has little or no catalyst vapor partial pressure. At a minimum, the scrubbing liquid has a catalyst vapor pressure less than that of the product stream 26. Suitable scrubbing liquids include, for example, organic starting material, intermediate product, product, fluorinations agent, and recycled liquid from the distillation unit.

The weight ratio of scrubbing liquid to product stream (herein "ratio") is low compared to the distillation unit. The ratio is relatively low because it is intended to scrub only those high-boiling components which are readily removable. The corrosive catalyst vapors tend to have high-boiling points and condense readily upon contact with the scrubbing liquid. Therefore, high ratios are not necessary.

Maintaining a low ratio is significant because, in the preferred embodiment, the scrubbing liquid along with the scrubbed catalyst returns to the reactor without pre-conditioning. Therefore, the returning liquid stream 24 reduces the heat available for reaction. A large ratio, hence high levels of scrubbing liquid, will overwhelm the heat inputs. Therefore, the ratio is preferably no greater than about 0.5/1, more preferably no greater than about 0.3/1, and even more preferably no greater than 0.2/1.

The amount of catalyst removed from the product stream depends upon the catalyst used and the ratio maintained. Naturally, the lowest possible catalyst content in the product stream is preferred. Higher catalyst concentrations result in a more corrosive product stream, and eventually the corrosion becomes too high for post-reaction processing apparatus such as reboilers. Additionally, higher catalyst concentrations require the distillation unit to remove more catalyst thereby reducing its effectiveness. The prescrubber, therefore, should remove preferably at least about 50% of the catalyst, more preferably at least about 75%, and even more preferably at least about 90%.

In the production of 245 fa, a ratio of about 0.2/1 corresponds to about 90% removal of antimony catalyst for the product stream. For comparison, traditional trichlorofluoromethane and chlorodifluoromethane manufacturing practice using liquid-phase antimony catalyst requires more than a 0.6/1 ratio in the distillation unit. The use of a pre-catalyst scrubber to remove catalyst needing only a low ratio is a distinction from past conventional antimony liquid-phase reactor design.

After leaving the prescrubber 12, the low-catalyst content product stream 26 enters the distillation unit 13 where it is separated into a low-boiling fraction stream 27 and a high-boiling point fraction stream 28. Suitable distillation units are well known in the art and include any conventional distillation apparatus. Commercially-available distillation apparatus include, for example, packed column units and tray column units such as those manufactured by Koch Engineering. In a preferred embodiment, the catalyst pre-scrubber and the distillation unit are constructed as a single column. In applications involving particularly corrosive catalysts, the distillation unit and its peripheral equipment are preferably lined, coated, or otherwise protected by a fluoropolymer.

In a preferred embodiment, the heat input needed to support distillation is provided by the reboiler 14 and not the reactor vessel 11. That is, rather than transferring heat into the reactor for distillation in excess of that needed for the reaction, as is the convention, the system of the present invention provides for a discrete reboiler 14 which provides the heat needed for distillation. The reboiler imparts this heat by vaporizing a portion of the high-boiling point fraction stream 28 and returning it to the distillation unit. Therefore, the only heat input for the reactor vessel is that needed for the reaction. This is a significant advantage over the prior art, especially for fluoropolymer lined reactors, since heat transfer through a fluoropolymer lined reactor is limited.

The implementation of the reboiler is possible due to corrosion reduction. The most significant reduction results from prescrubbing the product to form a low-catalyst content product stream as described above. In reactions where a antimony chloride catalyst is used, it has been found that corrosion may be further minimized in the reboiler by injecting chlorine in the high-boiling fraction stream 28. The chlorine reacts with the catalyst complex to form antimony pentachloride which tends to be a liquid and less corrosive at conventional distillation temperature ranges. Additionally, corrosion may be reduced by feeding the low-catalyst content product stream at the bottom of the column. This also tends to reduce the reboiling temperature.

The low-boiling fraction stream 27 enters a condenser 15 where a portion condenses and refluxes to the distillation unit, while the remaining portion leaves as the refined product stream 34. As mentioned above, conventional techniques are used to purify the desired product from the refined product stream. The details of this purification are not described herein since they are well known in the art.

As mentioned above, a preferred approach to adding heat to the reaction is by increasing the heat content of the reaction materials entering the reaction vessel 11. To this end, the present invention provides for a preconditioning system 10. Suitable preconditioner systems are commercially available and include, for example, standard shell and tube heat exchangers, available from, for example, Manning & Lewis (Union, N.J.). The preconditioning system may be a single integrated unit (as depicted in FIG. 1) or it may be several discrete units throughout the system 100, for example, each reactor feed material or stream may have its own discrete preconditioner. Furthermore, it should be noted that although two streams 21 and 22 are shown feeding the reactor, any number of streams are possible, each stream having a different heat content, for example, one stream may be more superheated than another.

Preconditioning ranges from preheating a liquid feed 21 to vaporizing and superheating a vapor feed 22. The degree of heat imparted to a reaction material depends considerably on its thermal stability. Many organic compounds, such as chlorinated hydrocarbons, which are used as organic starting materials for fluorinations, breakdown at temperatures below their boiling point. For example, when using HCC-240 fa as the organic starting material, the preheat temperature is likely to be limited to about 250° F. to minimize breakdown. For other reaction materials, such as HF and $Cl_2$, their thermal breakdown temperatures are much higher and they can be superheated well above their vaporization point. Absent thermal breakdown, higher temperatures are preferred up to about 350° F. which is just below the thermal property limits of many fluoropolymers.

The degree of preconditioning also depends upon the corrosive nature of the material. For example, in a preferred embodiment, the recycle stream 25 is preconditioned and fed to the reaction vessel 11. Rather than totally vaporizing this stream, however, it is preferred to partially vaporize it, for example, by about 80%, using the recycle vaporizer 16. The vaporized stream 31 can then be superheated, for example, to about 350° F., in the preconditioner system 10, and then fed to the reactor. By not completely vaporizing the recycle stream 25, we avoid concentrating catalyst or other corrosive material in the vapor, thus minimizing corrosion in the preconditioning 10 system. The liquid stream 32 having a relatively high catalyst concentration is returned to the reactor.

What is claimed is:

1. A process for producing a fluorinated organic compound comprising:

reacting an organic starting material with a fluorination agent in a fluoropolymer-lined reactor in the presence of a liquid-phase catalyst to produce a vaporized product stream;

scrubbing said vaporized product stream using a liquid stream of scrubbing agent to form a recycle stream comprising a liquid mixture of scrubbing agent and condensed catalyst and and a low-catalyst content product stream having a substantially lower concentration of catalyst than said vaporized product stream, wherein the weight ratio of said liquid stream of scrubbing agent to said vaporized product stream is no greater than about 0.5:1;

feeding a substantial portion of said recycle stream to said reactor; and recovering said fluorinated organic compound from said low-catalyst content stream.

2. The method of claim 1, wherein recovering said fluorinated organic compound comprises:

distilling said low-catalyst content product stream in a distillation unit to form a low-boiling point fraction and a high-boiling point fraction;

recovering said fluorinated organic compound from said low-boiling point fraction; and reboiling at least a portion of said high-boiling point fraction to form a vapor and returning said vapor to said distillation unit.

3. The method of claim 2, further comprising:

injecting chlorine into at least a portion of said high-boiling point fraction before reboiling.

4. The method of claim 2, further comprising:

feeding said low-catalyst content product stream at the bottom of said distillation unit.

5. The method of claim 2, further comprising:

using at least a portion of said high-boiling point fraction for scrubbing said product stream.

6. The method of claim 2, further comprising:

using at least a portion of said starting material for scrubbing said product stream.

7. The method of claim 2, wherein said process further comprises:

heating at least a portion of said high-boiling point fraction; and feeding the heated portion to the reaction.

8. The method of claim 7, wherein heating comprises:

partially vaporizing a portion of said high-boiling fraction to form a recycled vapor stream and a recycled liquid stream, said recycled liquid stream containing a relatively high content of catalyst compared to said recycled vapor stream.

9. The method of claim 8, wherein said process further comprises:

superheating said recycled vapor stream before feeding it to the reaction.

10. The method of claim 9, further comprising:

using at least a portion of said high-boiling point fraction for scrubbing said product stream.

11. The method of claim 10, further comprising:

feeding said low-catalyst content product stream at the bottom of said distillation unit.

12. A system for producing a fluorinated organic compound comprising:

a fluoropolymer-lined reactor adapted for reacting an organic starting material with a fluorination agent in the presence of a liquid-phase fluorination catalyst to produce a vaporized product stream;

a scrubber for scrubbing said vaporized product stream using a liquid stream of scrubbing agent to form an recycle stream comprising a liquid mixture of scrubbing agent and condensed catalyst and a low-catalyst content product stream having a substantially lower concentration of catalyst than said vaporized product stream;

wherein said scrubber is mounted atop said reactor, said scrubber and said reactor are configured such that said recycle stream is fed to said reactor, and the weight ratio of said liquid stream of scrubbing agent to said vaporized product stream is no greater than 0.5:1; and distillation apparatus for recovering said fluorinated organic compound from said low-catalyst content stream.

13. The system of claim 12, wherein means for recovering said fluorinated organic compound comprises:

a distillation unit for distilling said low-catalyst content product stream to form a low-boiling point fraction and a high-boiling point fraction;

means for recovering said fluorinated organic compound from said low-boiling point fraction; and a reboiler for reboiling at least a portion of said high-boiling point fraction to form a vapor for return to the distillation unit.

14. The system of claim 13, further comprising:

means for injecting chlorine into said high-boiling point fraction prior to said reboiler.

15. The system of claim 13, wherein said distillation unit is adapted to receive at least a portion of said low-catalyst content product stream at about its bottom.

16. The system of claim 13, wherein said means for scrubbing is adapted to receive at least a portion of said high-boiling point fraction for scrubbing said product stream.

17. The system of claim 13, wherein said means for scrubbing is adapted to receive at least a portion of said starting material for scrubbing said product stream.

18. The system of claim 13, further comprising:

a vaporizer for partially vaporizing a portion of said high-boiling fraction to form a recycled vapor stream and a recycled liquid stream.

19. The method of claim 1, wherein scrubbing comprises contacting said vaporized product stream with a scrubbing agent having a vapor pressure of catalyst less than that of said vaporized product stream.

20. The method of claim 1 wherein said the weight ratio of said liquid stream of scrubbing agent to said vaporized product stream is no greater than 0.5:1.

21. The method of claim 20 wherein said the weight ratio of said liquid stream of scrubbing agent to said vaporized product stream is no greater than 0.2:1.

22. The method of claim 19 wherein said scrubbing agent is selected from the group consisting of organic starting material, intermediate product, product, fluorinations agent, liquid from distillation of said low-catalyst content product stream, and combinations of two or more thereof.

23. The method of claim 20, wherein said the weight ratio of said liquid stream of scrubbing agent to said vaporized product stream is no greater than about 0.3:1.

24. The method of claim 1, wherein said recycle stream is gravity fed to said reactor.

25. The method of claim 1, wherein said catalyst is a pentavalent halide.

26. The system of claim 12, wherein said scrubber is mounted atop said reactor.

* * * * *